(12) United States Patent
Yamazaki et al.

(10) Patent No.: US 7,479,137 B2
(45) Date of Patent: Jan. 20, 2009

(54) LASER DEPILATOR

(75) Inventors: Iwao Yamazaki, Tokyo (JP); Akitsugu Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/515,829

(22) PCT Filed: Aug. 15, 2002

(86) PCT No.: PCT/JP02/08285

§ 371 (c)(1),
(2), (4) Date: Nov. 26, 2004

(87) PCT Pub. No.: WO03/101243

PCT Pub. Date: Dec. 11, 2003

(65) Prior Publication Data

US 2005/0177139 A1   Aug. 11, 2005

(30) Foreign Application Priority Data

May 31, 2002   (JP)   ............................. 2002-160767

(51) Int. Cl.
*A61B 18/20* (2006.01)
*A61N 5/067* (2006.01)

(52) U.S. Cl. .............................. 606/9; 606/133; 607/89

(58) Field of Classification Search ..................... 30/30, 30/34, 122; 606/9; 607/89
See application file for complete search history.

(56) References Cited

U.S. PATENT DOCUMENTS

| | | | | |
|---|---|---|---|---|
| 5,065,515 A | * | 11/1991 | Iderosa | 30/140 |
| 5,182,857 A | * | 2/1993 | Simon | 30/34.05 |
| 5,533,266 A | * | 7/1996 | Kelman | 30/122 |
| 5,606,798 A | * | 3/1997 | Kelman | 30/41.5 |
| 5,689,102 A | * | 11/1997 | Schonenberg et al. | 235/462.38 |
| 5,735,844 A | * | 4/1998 | Anderson et al. | 606/9 |
| 5,820,625 A | * | 10/1998 | Izawa et al. | 606/9 |
| 6,277,129 B1 | * | 8/2001 | Poran | 606/133 |
| 6,436,106 B2 | * | 8/2002 | Yiu | 606/133 |

(Continued)

FOREIGN PATENT DOCUMENTS

JP   2001-029124   2/2001

(Continued)

OTHER PUBLICATIONS

International Preliminary Examination Report, dated Aug. 14, 2004, issued in PCT Application No. PCT/JP2002/008285.

*Primary Examiner*—Henry M Johnson, III
(74) *Attorney, Agent, or Firm*—Finnegan, Henderson, Farabow, Garrett & Dunner, L.L.P.

(57) ABSTRACT

A laser depilator comprising a unit for removing hairs from the skin, a light source for irradiating laser light, and a lens for irradiating the skin with the laser light irradiated from the light source while deforming the beam shape so as to conform to the shape of a region of the skin from which hairs are removed by the hair removing unit. Since removal of hairs shielding the laser light and irradiation of laser light for damaging hair roots can be carried out continuously, efficiency of depilation treatment can be enhanced. Furthermore, depilation can be carried out effectively through a simple arrangement because a shaved skin surface can be irradiated with laser light over a relatively wide range using a lens.

10 Claims, 12 Drawing Sheets

U.S. PATENT DOCUMENTS

| | | | | |
|---|---|---|---|---|
| 6,485,484 | B1 * | 11/2002 | Connors et al. | 606/9 |
| 6,641,578 | B2 * | 11/2003 | Mukai | 606/9 |
| 7,204,832 | B2 * | 4/2007 | Altshuler et al. | 606/9 |
| 2003/0032950 | A1 * | 2/2003 | Altshuler et al. | 606/9 |
| 2004/0092959 | A1 * | 5/2004 | Bernaz | 606/131 |

FOREIGN PATENT DOCUMENTS

| | | |
|---|---|---|
| JP | 2001-094176 | 4/2001 |
| JP | 2001-238968 | 9/2001 |
| JP | 2002-506362 | 2/2002 |
| JP | 2002-065874 | 3/2002 |
| JP | 2003-126277 | 5/2003 |
| WO | WO 98/51235 | 11/1998 |
| WO | WO 99/46005 | 9/1999 |
| WO | WO 01/64285 | 9/2001 |

* cited by examiner

LASER DEPILATOR

TECHNICAL FIELD

The present invention relates to a laser depilator which irradiates the skin surface with laser light to perform a depilation treatment.

BACKGROUND ART

Laser light has a characteristic that it is reflected from a white substance but absorbed by a black substance. When it is irradiated to the skin surface of a human body, it is easily absorbed by melanin present in the skin. A principle of laser depilation irradiates laser light to cellular tissues of the skin containing a large amount of melanin, outer root sheaths, hair mother cells and the like to generate Joule heat so to damage hair roots, thereby destructing a hair regeneration mechanism.

To perform the laser depilation, it is necessary to remove previously hairs subject to the depilation before laser light is irradiated so that light energy is not mostly absorbed by hairs before laser light reaches the hair roots.

Hairs are removed by various methods such as pulling out hairs using tweezers, applying depilatory cream to a target portion, peeling hairs by a depilatory tape and the like. These depilatory methods are troublesome and also involve a pain but have advantages that the finish is fine because no hair remains as compared with shaving by a razor and the regrowth of hairs is delayed.

SUMMARY OF THE INVENTION

Laser depilatory is said that it must be performed continuously for a long period. For example, it is said that the effect can be obtained after a lapse of at least about three months after starting the depilation treatment by irradiation of laser light. Therefore, it is troublesome for the user to perform the above-described depilation treatment every time the laser depilation treatment is performed.

Under the circumstances described above, the present invention provides a laser depilator capable of performing a high-efficiency laser depilation treatment by a simple structure.

To achieve the above object, a laser depilator according to the present invention is comprised of a hair removing unit for removing hairs from the skin, a light source for irradiating laser light, and a lens for irradiating the skin with the laser light irradiated from the light source while deforming the beam shape so as to conform to the shape of the region of the skin from which hairs are removed by the hair removing unit.

This laser depilator can bring efficiency to the depilation treatment because the removal of hairs shielding the laser light and the irradiation of laser light damaging hair roots can be performed continuously. And, this laser depilator can use a lens to irradiate laser light to a relatively large range on the hair-removed skin surface and realize an effective depilation treatment by a simple structure.

For the hair removing unit, either a shaving mechanism for shaving the skin hairs or a mechanism for tweezing the skin hairs can be used.

When the shaving mechanism is used to remove hairs, a comfortable laser depilation treatment can be performed without damaging the skin and without causing substantially any pain. And, when the tweezing mechanism is used, there are advantages that substantially no hair remains unshaved, the finish is fine, and regrowth of hairs is delayed. The above mechanisms can be used selectively and appropriately for the hair removing unit.

The hair removing unit may be detachable from the laser depilator body.

The hair removing unit, which tends to become dirty because of the hairs removed from the skin, can be washed with water or the like by configuring it to be physically separable from an optical system and a control system for irradiating the laser light. As a result, the laser depilation treatment can be performed hygienically. And the hair removing unit can be prevented from being filled with hairs, and a good depilatory effect can be retained.

The laser depilator may further have a movement detection unit for detecting its movement with respect to the skin and an irradiation quantity control unit for controlling an irradiation quantity of laser light from the light source in response to the movement detected by the movement detection unit.

For the "movement detection unit", a roller which rotates in contact with the skin when the laser depilator is moved can be used. An optical method or the like may be used for the "movement detection unit" to detect the movement without contacting.

The detection of the movement of the laser depilator provides the following. For example, laser can be irradiated to the skin which is undergone the removal of hairs by the depilation unit by turning ON/OFF the laser light in accordance with the moving direction of the laser depilator. A nonuniform depilatory effect can be reduced by changing the intensity of the laser light in accordance with the moving speed of the laser depilator so to prevent the energy of laser light irradiated to the skin from varying largely.

The laser depilator may further have an image pickup unit for taking an image of at least proximity of an area of the skin to which laser light is irradiated through the lens and a display unit for magnifying and displaying the image taken by the image pickup unit.

The laser depilator body can be moved while seeing the magnified image of the portion being depilated displayed by the display unit, so that the laser light can be irradiated accurately to the target depilating portion. Thus, the depilatory effect is enhanced, the efficiency of the depilation treatment is improved, and the time and labor required for the depilation treatment are saved.

Because a visual change appears on the skin surface (particularly, a hair root cell portion) which is once exposed to the irradiation of the laser light, it is easy to distinguish between the portion irradiated with the laser light and the untreated portion. Thus, the efficiency of the treatment can be improved.

The laser depilator may be further provided with a recovery vessel for recovering hairs removed from the skin surface by the hair removing unit.

The removed hairs can be easily disposed because they can be collected into the recovery vessel.

The laser depilator may be further provided with a grip to be held by a user, and an operation unit disposed in proximity of the grip and to operate the irradiation of the laser light from the laser light source and the hair removing unit.

For example, it becomes possible to operate by one hand, and the laser depilator becomes excellent in convenience.

The hair removing unit may have a plural-blade unit.

The hair removing unit, e.g., the shaving mechanism, is comprised of so-called double blades or triple blades, so that hairs are shaved deeply, and the hair root portions are well exposed. Thus, the laser light energy can be supplied to the hair root portions in a larger quantity, and the depilatory effect can be enhanced.

Here, the hair root portions buried deep into the skin are substantially pulled up to the skin surface by the blade unit at the moment of shaving hairs by the third blade or the like, so that the hair root portions to which the laser light is irradiated then is largely damaged, and a high-efficiency depilation treatment is performed.

The power supply for driving the device body may be a rechargeable battery or a dry cell. This laser depilator is suitable as, for example, a portable device.

A depilation treatment adjusting mechanism, which varies a drive speed of the hair removing unit and an irradiation power of the laser light by the laser irradiation mechanism and adjusts the distribution between them, may be further provided.

When the drive speed of the hair removing unit is set to be fast, namely an effect of removing unwanted hairs is high (the energy of laser light is hardly absorbed by unwanted hairs), the laser depilator according to the present invention adjusts the irradiation power of laser light to be weak. Meanwhile, when the drive speed of the hair removing unit is set to be slow, namely when the effect of removing unwanted hairs is low (the energy of laser light is easily absorbed by the unwanted hairs), the irradiation power of laser light is adjusted to be high. Therefore, this laser depilator uses power effectively and is economical. When a rechargeable battery or a dry cell is used as the drive power supply, the laser depilation treatment can be performed for a long time.

The laser depilator may be provided with an irradiation power display unit which visually indicates the irradiation power of the laser light irradiated from the laser light source.

The irradiation energy of laser light to the skin surface which is significant as a depilation treatment condition can be made recognizable by the user.

A laser depilator according to the present invention is comprised of a hair removing unit for removing hairs from the skin, a light source for irradiating laser light, a condenser lens for condensing light irradiated from the light source, and an irradiation position changing mechanism for displacing an irradiation spot of light condensed by the condenser lens.

The irradiation range of the laser light can be dissipated (expanded) by giving, for example, weak vibrations or a reciprocating motion to the laser light source or the condenser lens. Thus, a high-efficiency laser depilation treatment can be realized by a simple structure.

A laser depilator according to the present invention is comprised of a~hair removing unit for removing hairs from the skin, a light source for irradiating laser light, a condenser lens for condensing light irradiated from the light source, and a light guiding member for dividing the laser light condensed by the condenser lens into plural luminous fluxes and guiding them to irradiate the skin.

By using the light guiding member which divides the laser light into plural luminous fluxes and guiding them to irradiate the skin, the laser light can be irradiated to a relatively large range on the skin surface where hairs have been removed by the hair removing unit, and a high-efficiency depilation treatment can be realized by a simple configuration.

BEST MODE FOR CARRYING OUT THE INVENTION

Embodiments of the present invention will be described with reference to the accompanying drawings.

First Embodiment

Figure 1:
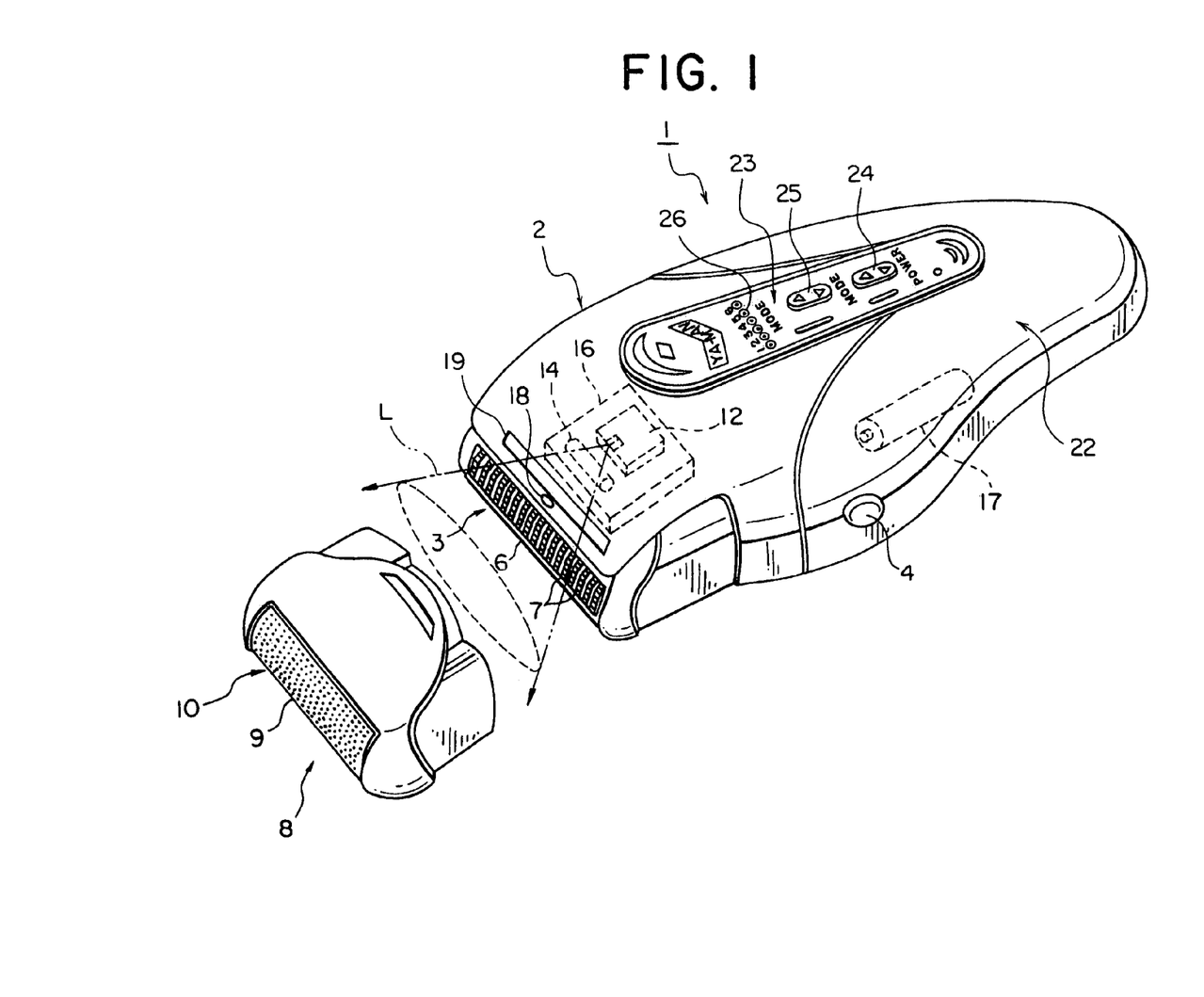
FIG. 1 is a perspective diagram showing the laser depilator according to a first embodiment of the present invention.

FIG. 1 is a perspective diagram showing the laser depilator according to the first embodiment of the invention.

Figure 2:
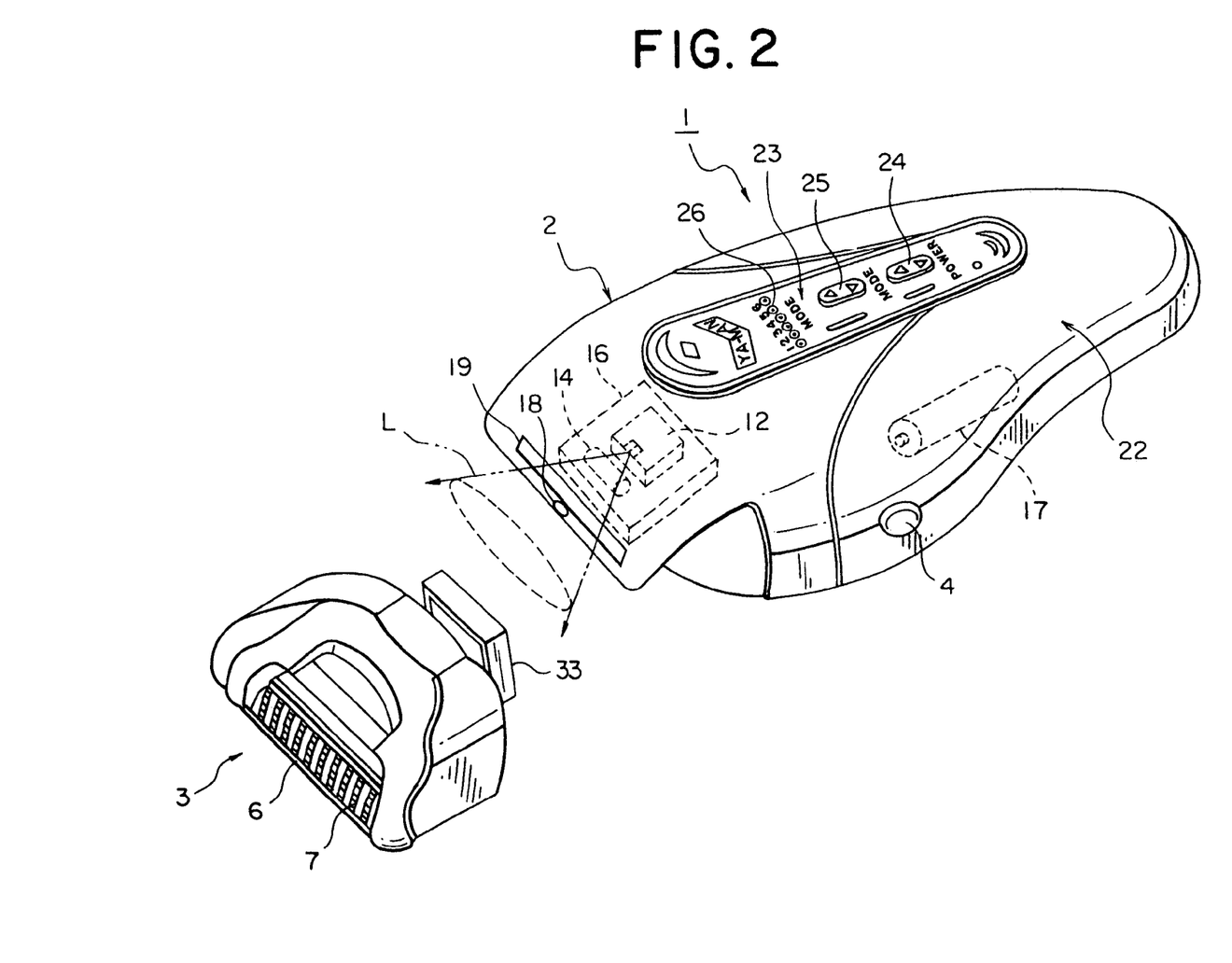
FIG. 2 is a perspective diagram showing a state of the laser depilator of FIG. 1 with a tweezer head unit removed from the laser depilator body.
Figure 3:
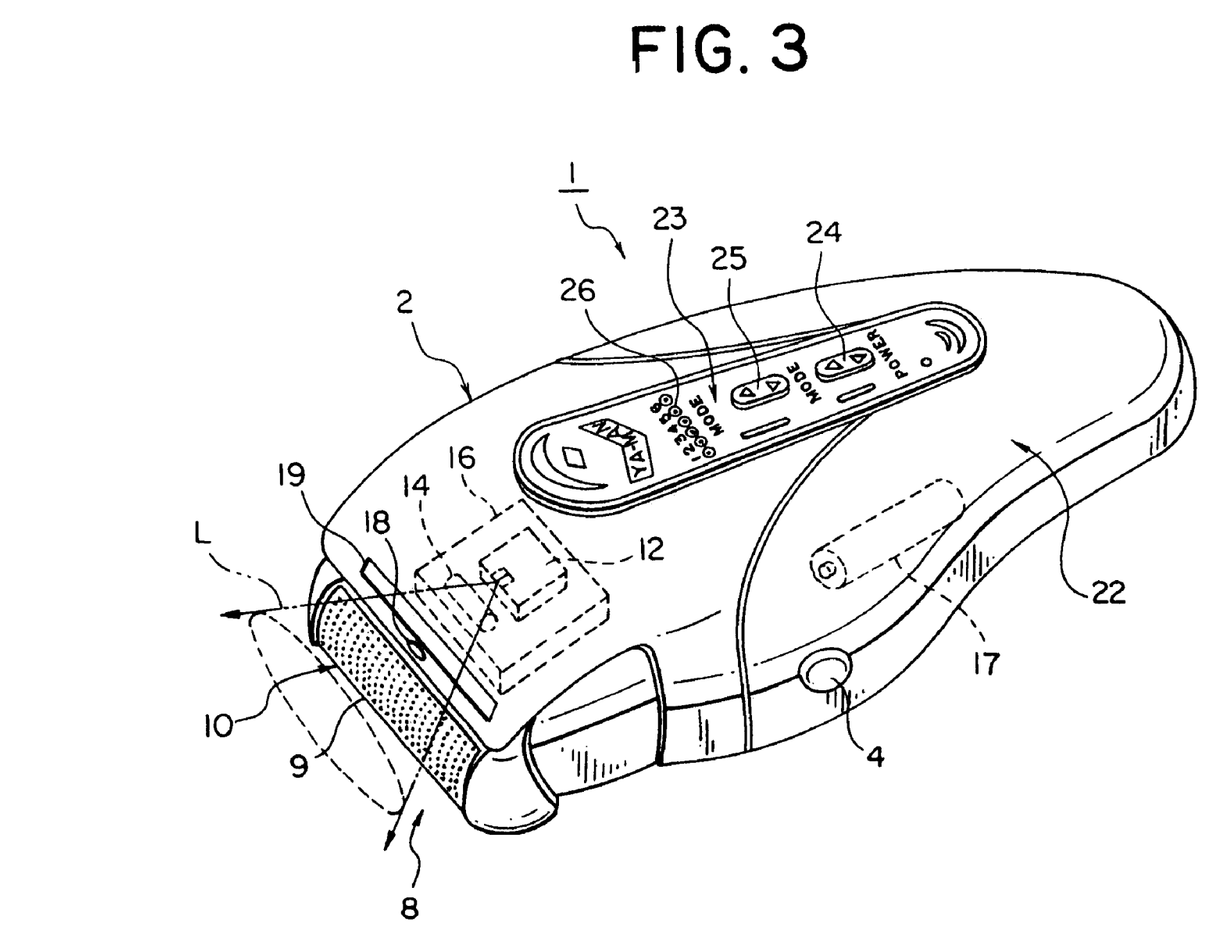
FIG. 3 is a perspective diagram showing a state of the laser depilator of FIG. 1 with a shaving head unit attached to the laser depilator body.
Figure 4:
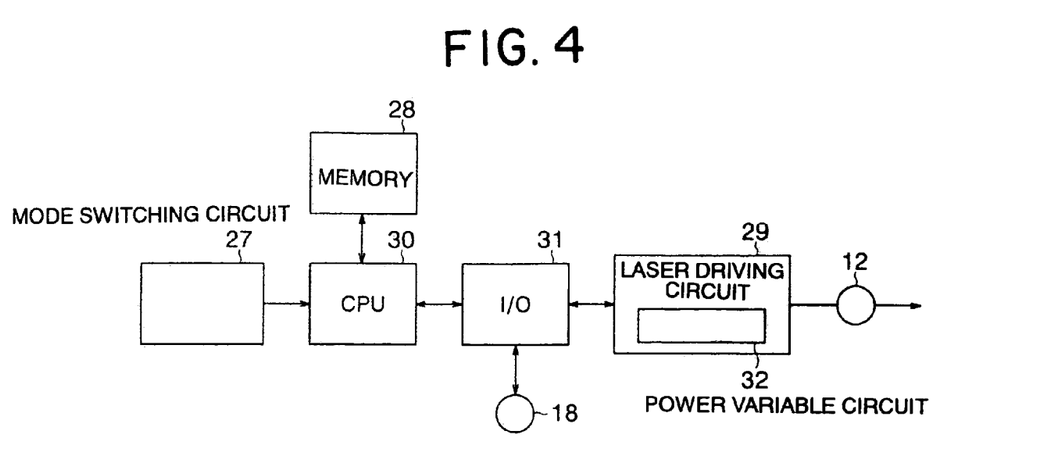
FIG. 4 is a functional block diagram showing a control system of the laser depilator of FIG. 1.
Figure 5:
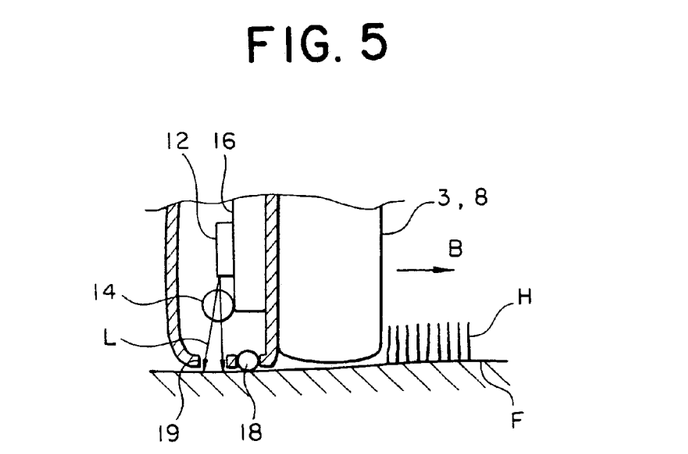
FIG. 5 is a partially sectional diagram showing a state of depilating by the laser depilator of FIG. 1.
Figure 6:
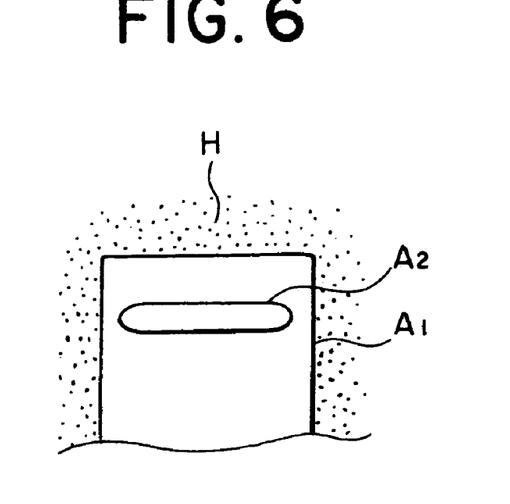
FIG. 6 is a plan diagram showing the skin surface under depilation treatment by the laser depilator of FIG. 1.

FIG. 2 is a perspective diagram showing a state of the laser depilator of FIG. 1 with a tweezer head unit removed from the laser depilator body, FIG. 3 is a perspective diagram showing a state of the laser depilator of FIG. 1 with a shaving head unit attached to the laser depilator body, and FIG. 4 is a functional block diagram showing a control system of the laser depilator of FIG. 1. FIG. 5 is a partially sectional diagram showing a state of depilating by the laser depilator of FIG. 3, and FIG. 6 is a plan diagram showing the skin surface under depilation treatment by the laser depilator of FIG. 3.

As shown in FIG. 1 to FIG. 3, this laser depilator 1 is used by a user oneself to perform a laser depilation treatment (laser depilation treatment) and comprised of a laser depilator body 2, a tweezer head unit 3 and a shaving head unit 8 which are detachable from the laser depilator body 2. The head unit can be removed from the laser depilator body 2 by pulling the head unit to separate from the laser depilator body 2 while depressing a pair of unlocking buttons 4 (one of them is not shown).

The tweezer head unit 3 and the shaving head unit 8 which tend to get dirty because of the tweezed hairs and the shaved hairs can be washed because they can be removed from the laser depilator body 2 having an optical system for irradiating laser light and the control system.

The tweezer head unit 3 has a tweezing mechanism 7 for tweezing hairs from the skin surface to which a front 6 of the head unit is contacted. The tweezing mechanism 7 has, for example, plural pinching claws on the peripheral surface of a rotatable cylindrical member. The pinching claws each are configured of a pair of plates, which repeats a contact and separate operation in synchronization with the rotations of the cylindrical member. The tweezing mechanism 7 may be configured of a group of rollers which catches hairs and rotates to pull out. A current of a high frequency of approximately 300 to 3000 Hz may be fed to the rollers to denaturalize the protein of papilla pili portions so as to improve the depilatory effect.

Meanwhile, the shaving head unit 8 is provided with a shaving mechanism 10 for shaving hairs on the skin surface to which a front 9 of the head unit is contacted. The shaving mechanism 10 adopts, for example, a vibration-type shaving mechanism, and comprises an outside blade configuring the front 9 of the head unit and an inside blade which vibrates within the outside blade. The shaving mechanism 10 may adopt a rotary-type shaving mechanism of shaving hairs by rotating the inside blade instead of the vibration type.

As shown in FIG. 2, an unwanted hair recovery case 33 for recovering hairs removed from the skin surface is disposed in a detachable portion between the tweezer head unit 3 or the shaving head unit 8 and the laser depilator body 2. Thus, the unwanted hairs removed from the skin surface can be disposed with ease.

The tweezing mechanism 7 and the shaving mechanism 10 are operated by a driving force transmitted from the laser depilator body 2.

Use of either the tweezer head unit 3 or the shaving head unit 8 is preferably determined appropriately depending on a portion to be depilated. When the tweezer head unit 3 is used, a good depilatory effect can be obtained because the skin surface after the removal of hairs is smooth and the regrowth of hairs is delayed. Meanwhile, when the shaving head unit 5 is used, the depilatory effect is slightly lowered, but a comfortable laser depilation treatment can be performed without damaging the skin or hardly causing a pain. The head unit may be provided with a roller so to facilitate the movement of the head unit on the skin surface, and this roller can be used as a roller 18 to be described later.

The laser depilator body 2 has a laser diode 12, a cylindrical lens 14, a heat sink 16, a battery 17 and the roller 18 therein and has an opening 19 formed as shown in FIG. 1 to FIG. 3.

The cylindrical lens 14 changes the sectional shape of the beam of laser light L irradiated from the laser diode 12 from a substantially circular shape to a substantially oval shape. This is to comply with an area of the skin where hairs are removed by the head unit.

The laser depilator 1 is held by a hand and moved on the skin as shown in FIG. 5 so to remove hairs H in a belt-shaped area A1 in a moving direction as shown in FIG. 6. The laser light passed through the cylindrical lens 14 is irradiated to an area A2 in the hair-removed area A1 to form an irradiation spot.

The shape of the cylindrical lens 14 may be either a cylindrical shape with convex sides or a semicylindrical shape with convex and flat sides. An ellipsoidal lens can also be used instead of the cylindrical lens 14. The cylindrical lens 14 serves to deform the cross-sectional shape of the beam of laser light from the substantially circular shape to a long and thin shape such as a substantially oval shapes and an appropriate optical element (e.g., a prism) can be used instead of the cylindrical lens 14 in a range satisfying such a role.

The heat sink 16 dissipates heat generated at the operation of the laser diode 12 by heat conduction to suppress the performance from being degraded by the temperature increase. Therefore, the heat sink 16 is formed of aluminum or its alloy having good heat conductivity, and a single or plural through holes are formed to increase the surface area so as to enhance the heat radiation effect. Besides, the heat sink 16 can be configured to be a housing-integral heat sink by integrally forming with the housing of the laser depilator body 2.

The laser diode 12 is an example of the laser light source and, for example, a semiconductor device capable of irradiating laser light having a wavelength of 600 to 1600 nm and light output of 5 mW to 9 W can be used. Specifically, a PN-junction diode using a compound semiconductor such as GaAs (gallium arsenide) is used for the laser diode 12, and an electric current is directly passed to it for excitation. Thus, laser oscillation can be obtained.

The battery 17 is a power supply, such as a rechargeable battery or a dry cell, for driving the laser depilator.

The roller 18 is a detection means for detecting the movement of the laser depilator body 2 on the skin. As shown in FIG. 5, it is desirable that the laser depilator body 2 is moved in a moving direction B to remove hairs H from the skin by the head unit, then the laser light is irradiated. When the laser depilator body 2 is moved in a direction opposite to the direction B, the laser light is irradiated to the skin surface where hairs H have not been removed.

Therefore, as a moving direction of the laser depilator 1 on the skin is detected by the roller 18, when the laser depilator 1 is moving in the direction B of FIG. 5, the laser light is irradiated, and when the laser depilator 1 is moving in the opposite direction, the irradiation of the laser light is stopped, useless irradiation of the laser light can be decreased.

The moving speed of the laser depilator 1 may be detected by the roller 18 to vary the intensity of the irradiated laser light depending on the moving speed. When the moving speed of the laser depilator 1 is low, a total amount of energy of the laser light irradiated to the skin increases even when the intensity of the irradiated laser light is not so high. Meanwhile, when the moving speed of the laser depilator 1 is high, the total amount of energy of the laser light irradiated to the skin tends to become small. Therefore, uneven irradiation onto the skin can be prevented by controlling the intensity of the laser light in accordance with the moving speed of the laser depilator 1.

The roller 18 may be attached to the head unit instead of the laser depilator body 2.

The opening 19 is a window for allowing the passage of the laser light irradiated to the skin and, if necessary, a light-transmittable material or the cylindrical lens 14 can be filled in it.

As shown in FIG. 1, the laser depilator 1 has a grip 22 which is formed with its profile partly depressed so to facilitate the holding by a user and an operation unit 23 which is disposed in proximity to the grip 22 to operate the irradiation of the laser light from the laser diode 12, the tweezing mechanism 7 and the shaving mechanism 10.

The operation unit 23 is mainly comprised of a power switch 24 for turning on/off the power of the device body, a mode setting switch 25 for setting an operation mode of laser depilation, and an LED 26 visually indicating the set mode.

The laser depilator 1 can be manipulated in various ways by one hand because the operation unit 23 is disposed in proximity to the grip 22, and it is excellent in convenience as, for example, a portable device.

The LED 26 may also be used as an indicator for visually indicating the irradiation power of the laser light irradiated from the diode 12. Thus, the irradiation energy of the laser light to the skin surface, which is significant as a depilation treatment condition, can be made recognized by the user, and the depilation treatment conditions can be set accurately.

Then, the control system of the laser depilator 1 will be described.

Specifically, the control system of the laser depilator 1 is comprised of a mode-switching circuit 27, a memory 28, a laser driving circuit 29, a CPU 30 and an interface 31 as shown in FIG. 4.

The contents set by the mode setting switch 25 are input to the mode-switching circuit 27.

Various set values and programs, such as an irradiation pattern of the laser light, the drive pattern of the tweezing mechanism 7 and the shaving mechanism 10, are stored in the memory 28. Specific set values includes a set value of irradiation timing of laser light intermittently irradiated from the laser diode 12 at a prescribed time interval, set values of irradiation power (output levels) of laser light corresponding to the set contents of the mode setting switch 25 and a set value of a drive speed of the tweezing mechanism 7 or the shaving mechanism 10.

The irradiation power set value of the laser light stored in the memory 28 can be set according to the drive speed of the tweezing mechanism 7 or the shaving mechanism 10. When the drive speed of the tweezing mechanism 7 or the shaving mechanism 10 is set to be high, namely when an effect of removing unwanted hairs is high (when laser light energy is hardly absorbed by unwanted hairs), it is set to decrease, for example, the irradiation power of the laser light.

When the tweezing mechanism 7 or the shaving mechanism 10 is set to have a low drive speed, namely when the effect of removing unwanted hairs is low (when the laser light energy is easily absorbed by unwanted hairs), it is set to increase the laser light irradiation power. Thus, the power is effectively used, and the device can be used for a long time.

Information indicating the relationship between ON/OFF of laser light and the intensity of the irradiated light corresponding to the moving direction and moving speed of the laser depilator detected by the roller 18 is also stored as configuration information in the memory 28. And, information indicating whether the intensity of the laser light is controlled in accordance with the movement detected by the roller 18 can also be included in the configuration information.

The laser driving circuit 29 controls the emission of the laser light from the laser diode 12. Specifically the laser driving circuit 29 supplies the laser diode 12 with a prescribed drive current voltage under control by the CPU 30 to emit the laser light from the laser diode 12. The laser driving circuit 29 has a laser power variable circuit 32 for controlling a voltage (current value) to be supplied to the laser diode 12. Specifically, the laser power variable circuit 32 adjusts the power of laser light emitted by the laser diode 12 in accordance with the configuration contents by the mode setting switch 25.

The CPU (Central Processing Unit) 30 exercises centralized control of the mode-switching circuit 27, the memory 28, the laser driving circuit 29 and the interface 31.

The interface 31 connects the laser driving circuit 29, the roller 18 and the CPU 30.

When the above-configured laser depilator 1 is used to actually perform a depilation treatment, by the power switch 24 and the mode setting switch 25, its power is turned on and an operation mode of the laser depilation is selected appropriately. Then, the tweezer head unit 3 or the shaving head unit 8 of the laser depilator 1 is pressed against the skin surface, and the head unit is slowly moved on the skin surface as shown in FIG. 5.

Thus, laser light is irradiated to the area A2 in the area A1 on the skin surface where the unwanted hairs are shaved or tweezed as shown in FIG. 6.

In this case, the depilation treatment to be performed before the laser depilation treatment and the irradiation of the laser light for damaging hair roots can be performed continuously, so that the depilation treatment can be made efficient.

And, the laser depilator 1 has the cylindrical lens 14 to irradiate the laser light to a relatively large range on the hair-tweezed (-shaved) skin surface. Thus, an effective depilation treatment can be achieved by a simple configuration.

Besides, the intermittence or irradiation intensity of the laser light can be controlled by the roller 18 according to the moving direction or the moving speed of the laser depilator 1. Therefore, laser light can be securely irradiated to the hair-removed skin surface, and a quantity of irradiation to the skin can be controlled appropriately depending on the speed.

Figure 7:
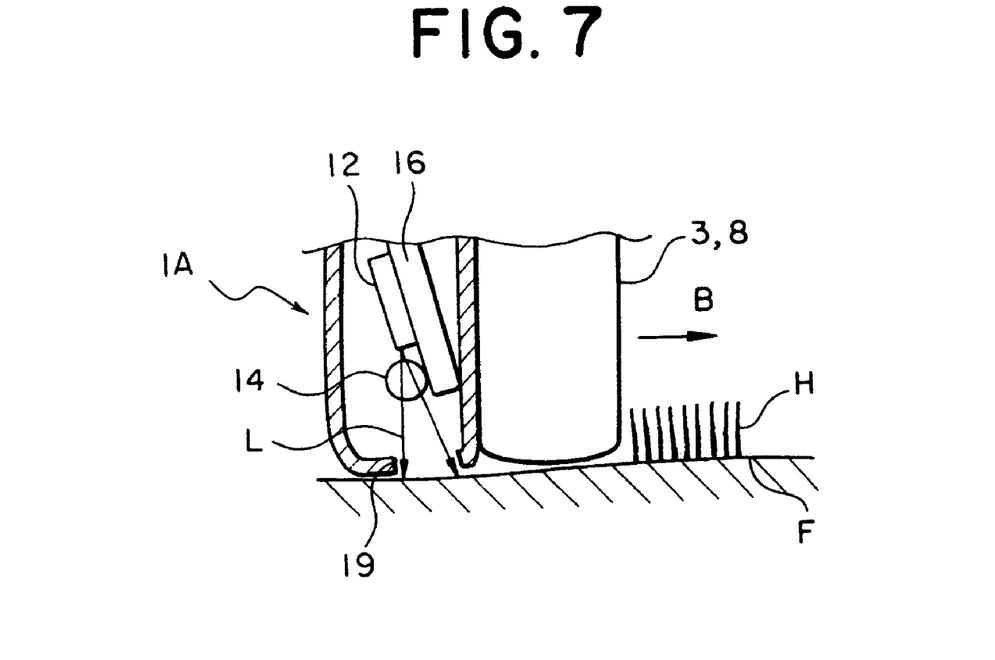
FIG. 7 is a partially sectional diagram showing a state of depilating by the laser depilator according to a modified embodiment of the first embodiment of the invention.

FIG. 7 is a partially sectional diagram showing a state of depilating by a laser depilator 1A according to a modified embodiment of the first embodiment of the present invention and corresponds to FIG. 5.

In the laser depilator 1A, the laser diode 12 is slantingly disposed with respect to the laser depilator body 2. Consequently, the laser light is irradiated to the skin surface closer to the head unit as compared with the one shown in FIG. 5. Specifically, the laser light is irradiated by the laser diode 12 to the skin immediately after the removal of hairs by the head unit.

The configuration that the irradiation spot of laser light is made closer to the head unit can also be realized by a method other than the method of inclining the laser diode 12. For example, it can be realized by changing the shape of the cylindrical lens 14 from a cylindrical shape to an asymmetrical shape on the sheet of FIG. 7. It can also be realized by using an appropriate optical device such as a prism or a light guiding member such as an optical fiber.

FIG. 7 does not show the roller 18, which may be disposed appropriately in the laser depilator body 2 or the head unit.

Second Embodiment

Figure 8:
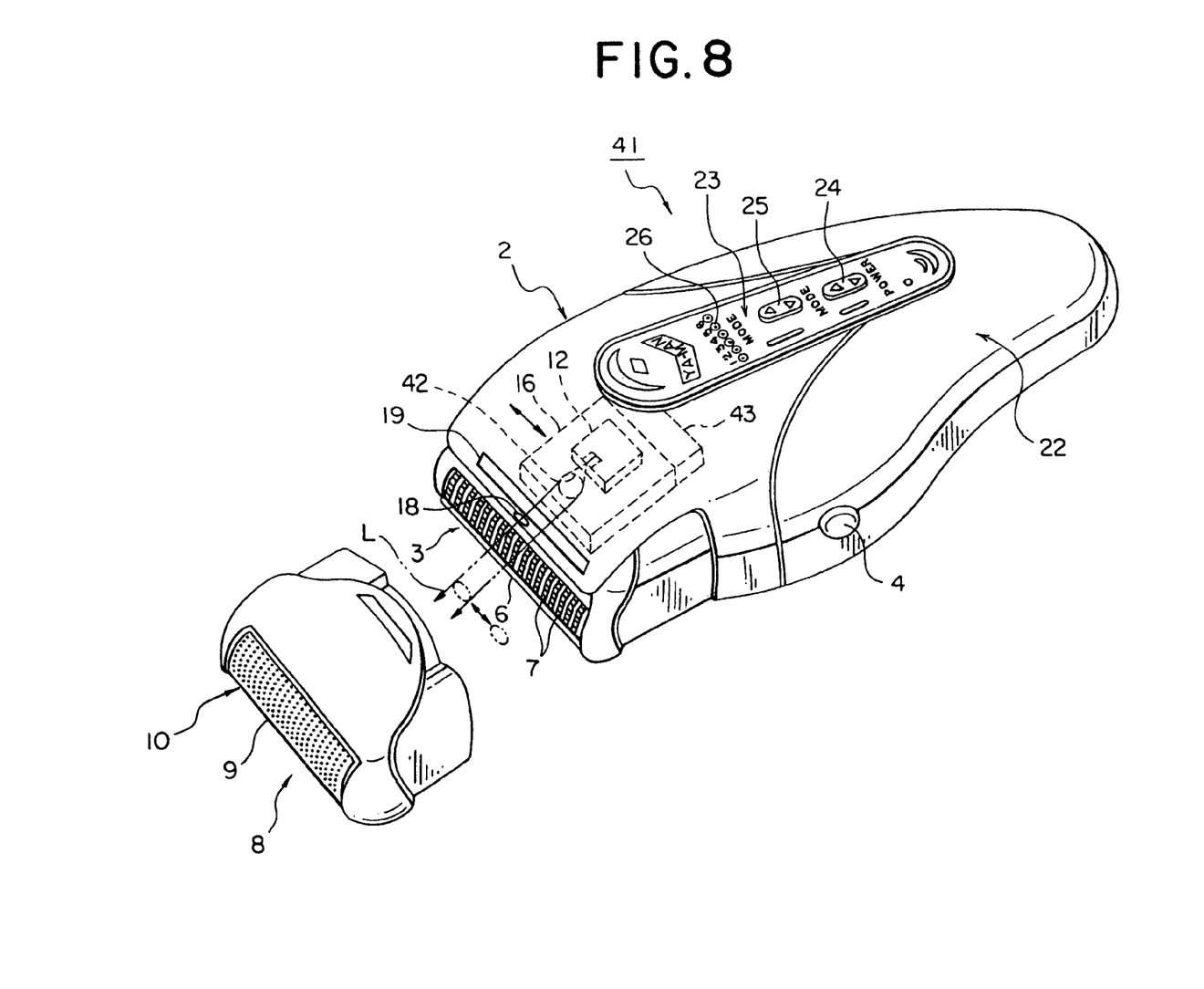
FIG. 8 is a perspective diagram showing the laser depilator according to a second embodiment of the invention.

FIG. 8 is a perspective diagram showing a laser depilator 41 according to the second embodiment of the present invention. The laser depilator 41 has a spherical lens 42 instead of the cylindrical lens 14 and also an irradiation position changing unit 43 for changing the irradiated position of laser light.

The spherical lens 42 functions as a condenser means for condensing the laser light.

The irradiation position of the laser light is changed with time by the irradiation position changing unit 43. Then, as a time-average, the laser light can be irradiated to a flat area proximate to the area A2 shown in FIG. 6.

The irradiation position changing unit 43 is comprised of, for example, an eccentric motor or the like and vibrates (reciprocally moves) the laser diode 12 and the spherical lens 42 together with the heat sink 16. The laser diode 12 and the spherical lens 42 are integrally displaced to keep the condensed state by the spherical lens 42 constant. The irradiation position changing unit 43 can be comprised of a combination of rack-and-pinion and a forward-reversal rotation switching motor or appropriate use of a crankshaft mechanism or the like if it can produce a reciprocating motion.

The laser light L can be dissipated (to expand the irradiation range of the laser light L) by the spherical lens 42 and the irradiation position changing unit 43, and a high-efficiency laser depilation treatment can be realized by a simple configuration.

Figure 9:
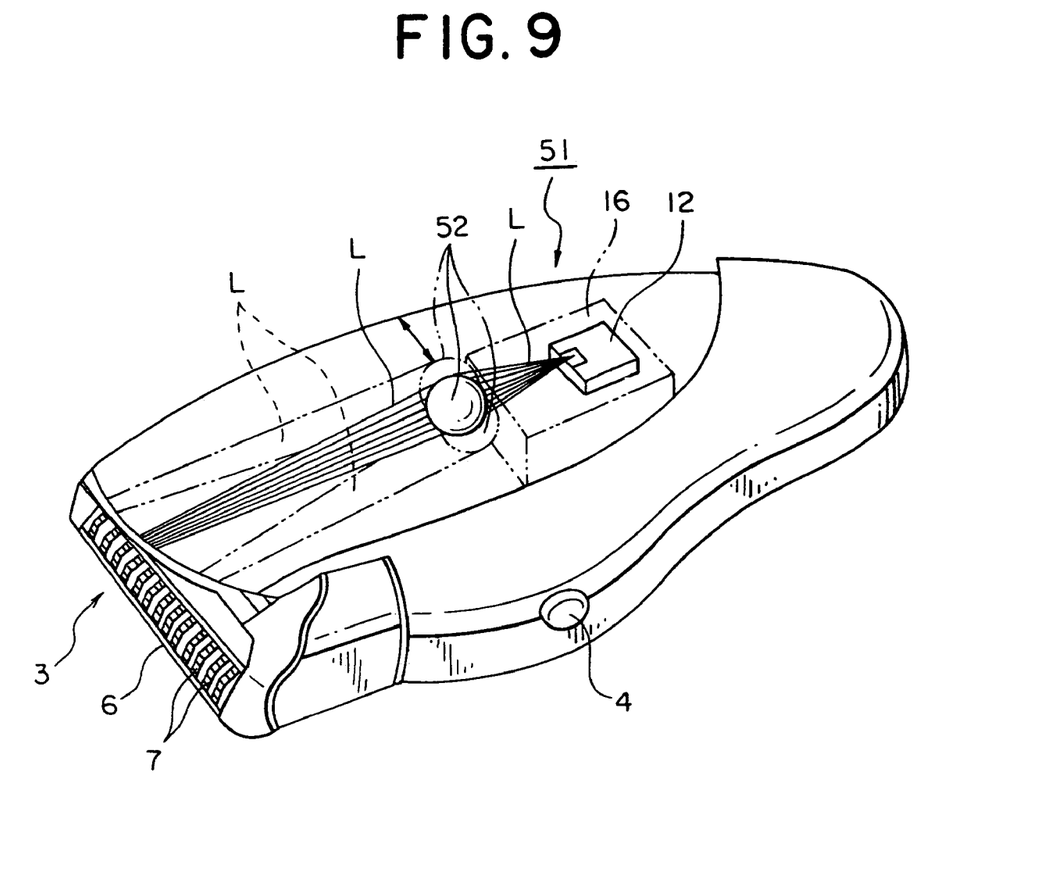
FIG. 9 is a perspective diagram showing the laser depilator partly broken away according to a modified embodiment of the second embodiment of the invention.

FIG. 9 is a perspective diagram showing a laser depilator 51 partly broken away according to a modified embodiment of the second embodiment.

The laser depilator 51 according to this modified embodiment uses, for example, an eccentric motor or the like to give weak vibrations to only a spherical lens 52. Thus, the laser light L can be dissipated by vibrating the spherical lens 52 with the laser diode 12 fixed. Conversely, the laser light L can also be dissipated by vibrating the laser diode 12 with the spherical lens 52 fixed.

Third Embodiment

Figure 10:
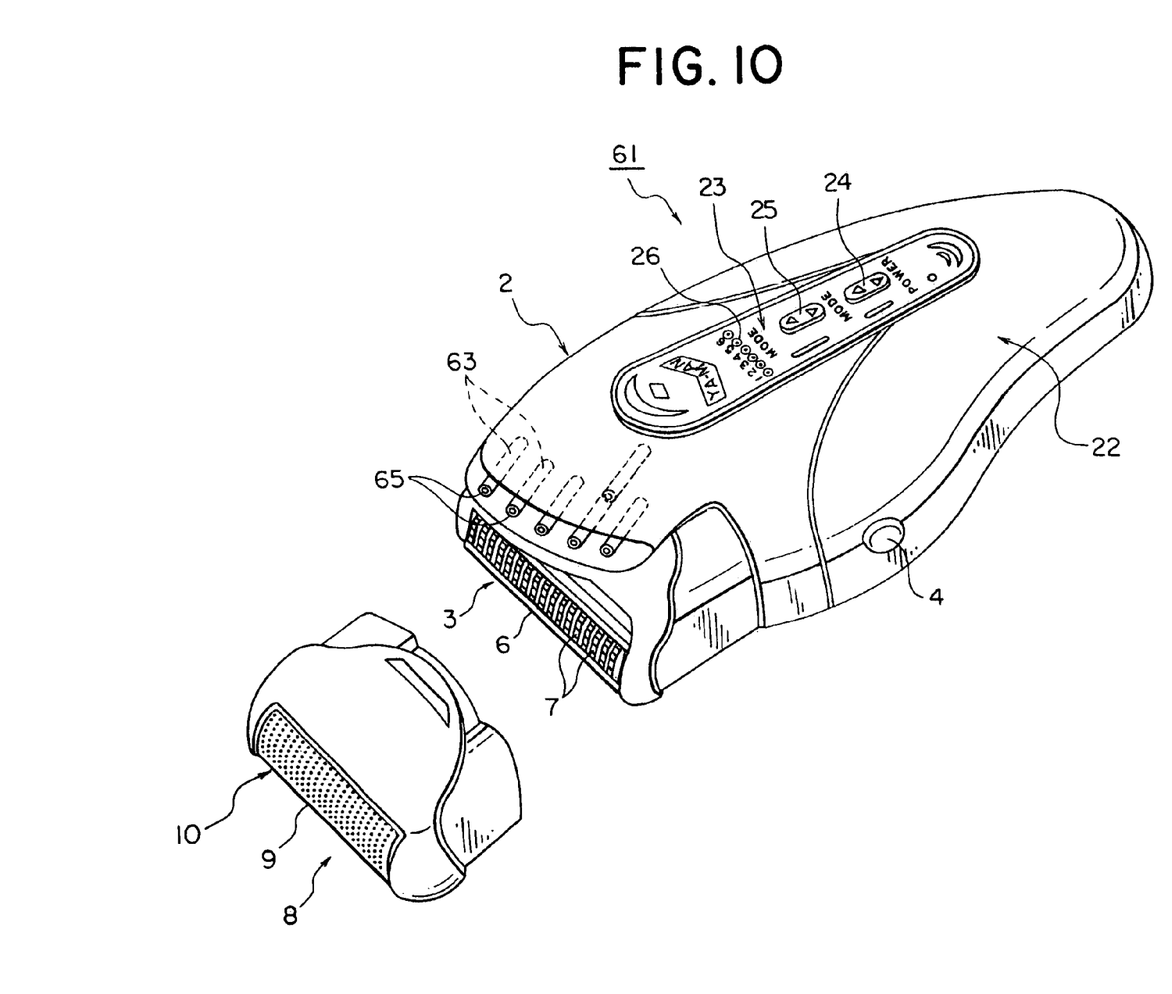
FIG. 10 is a perspective diagram showing the laser depilator according to a third embodiment of the invention.
Figure 11:
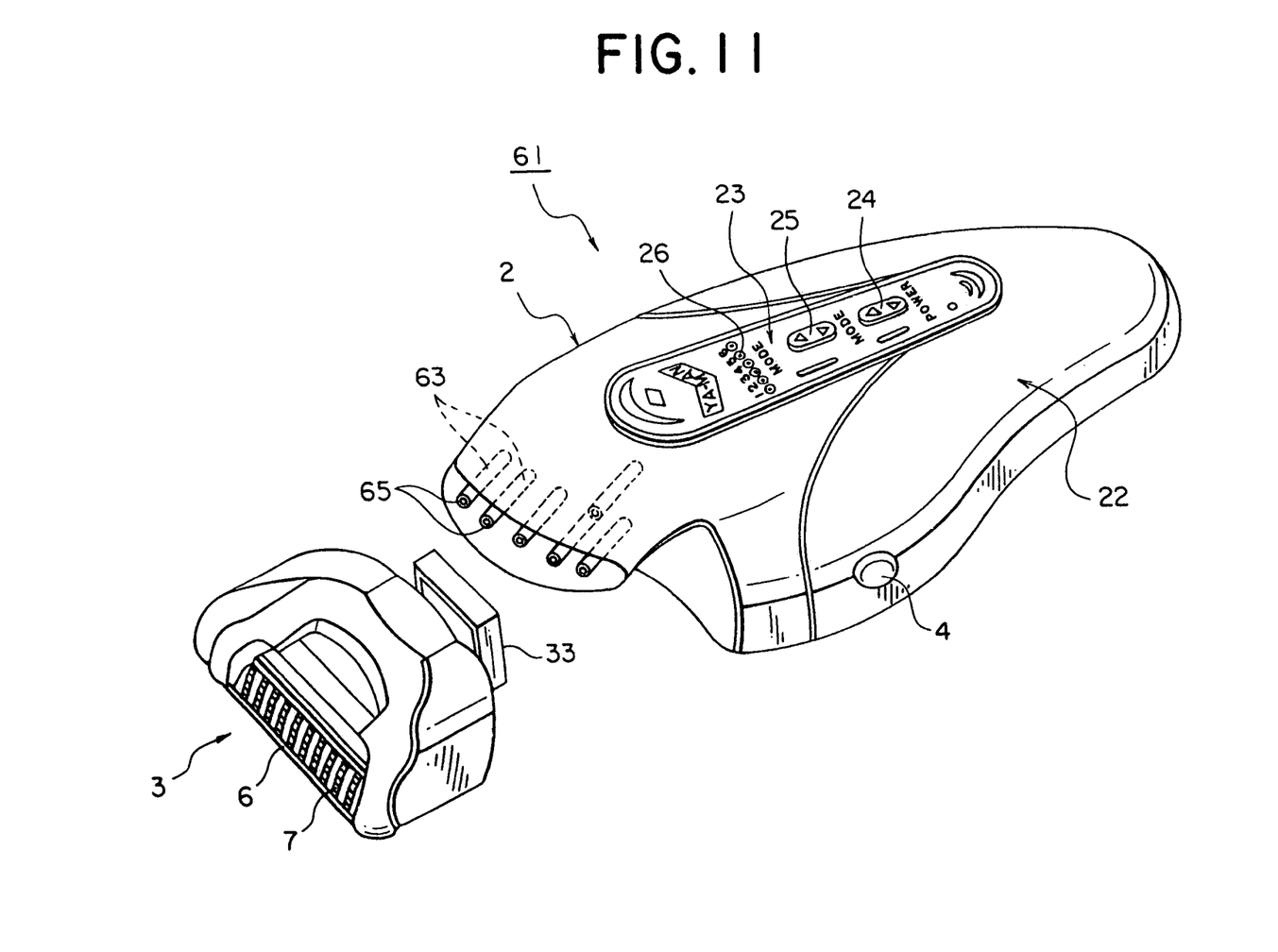
FIG. 11 is a perspective diagram showing a state of the laser depilator of FIG. 10 with a tweezer head unit removed from the laser depilator body.
Figure 12:
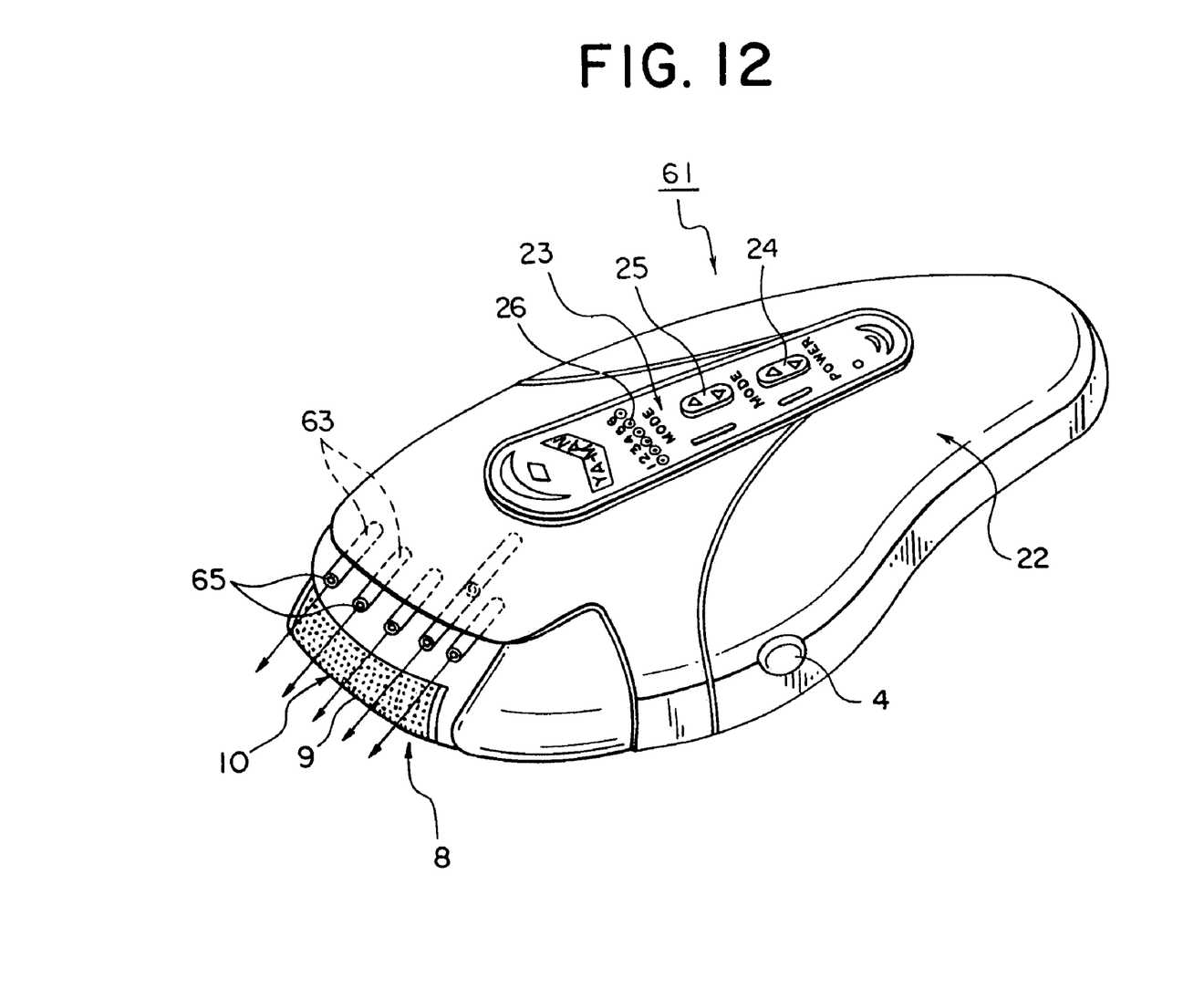
FIG. 12 is a perspective diagram showing a state of the laser depilator of FIG. 10 with the shaving head unit attached to the laser depilator body.
Figure 13:
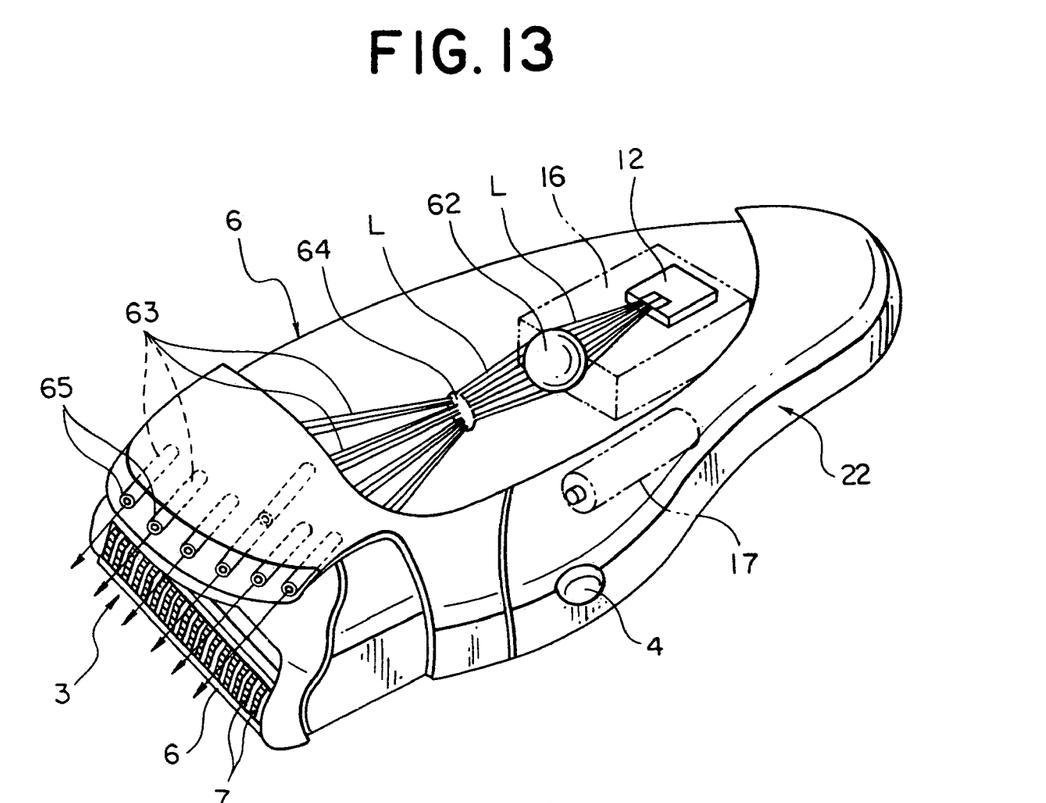
FIG. 13 is a perspective diagram showing the laser depilator of FIG. 10 partly broken away.

FIG. 10 to FIG. 12 are perspective views showing a laser depilator 61 according to the third embodiment of the present invention and correspond to FIG. 1 to FIG. 3 showing the first embodiment. FIG. 13 is a perspective diagram showing the laser depilator 61 partly broken away.

As shown in FIG. 10 to FIG. 12, the laser depilator 61 is comprised of the laser depilator body 2, the tweezer head unit 3 which is detachable from the laser depilator body 2, and the shaving head unit 8 in the same manner as in the first and second embodiments.

As shown in FIG. 13, the laser depilator body 2 has therein the laser diode 12, a spherical lens 62, optical parts comprising plural optical fibers 63 as the light guiding member, the heat sink 16 and the battery 17.

The spherical lens 62 condenses the laser light L irradiated from the laser diode 12.

The plural optical fibers 63 are radially disposed to receive the laser light L condensed by the spherical lens 62 through individual base portions 64 and to divide the received laser light L into plural luminous fluxes. The plural optical fibers 63 guide the laser light L which is divided into the plural luminous fluxes and irradiate the laser light, (divided into plural luminous fluxes) L from individual leading ends 65 to the skin surface to which the tweezer head unit 3 or the shaving head unit 8 is contacted or its vicinity (see FIG. 12, FIG. 13).

Figure 14:
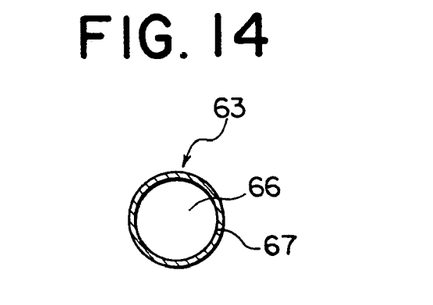
FIG. 14 is a sectional diagram showing an optical fiber configuring a part of the optical system of FIG. 13.

As shown in FIG. 14, the optical fiber 63 has the peripheral surface of an acrylic core 66 coated with fluorocarbon resin or the like as a clad 67. The optical fibers 63 may also be formed of multicomponent glass, quartz glass or the like. The laser depilator may be configured in such a way that a household AC power supply can be used as the drive power supply instead of the battery 17.

The laser depilator 61 irradiates laser light to a relatively large range of the skin surface where hairs have been tweezed (shaved) by means of the tweezing mechanism (or shaving mechanism 10) 7 for tweezing hairs from the skin surface, the spherical lens 62 for increase the light energy density of the laser light and the optical fibers 63 for dividing the laser light having the energy density increased into plural, luminous fluxes. Thus, an effective depilation treatment can be performed by a simple structure.

Fourth Embodiment

Figure 15:
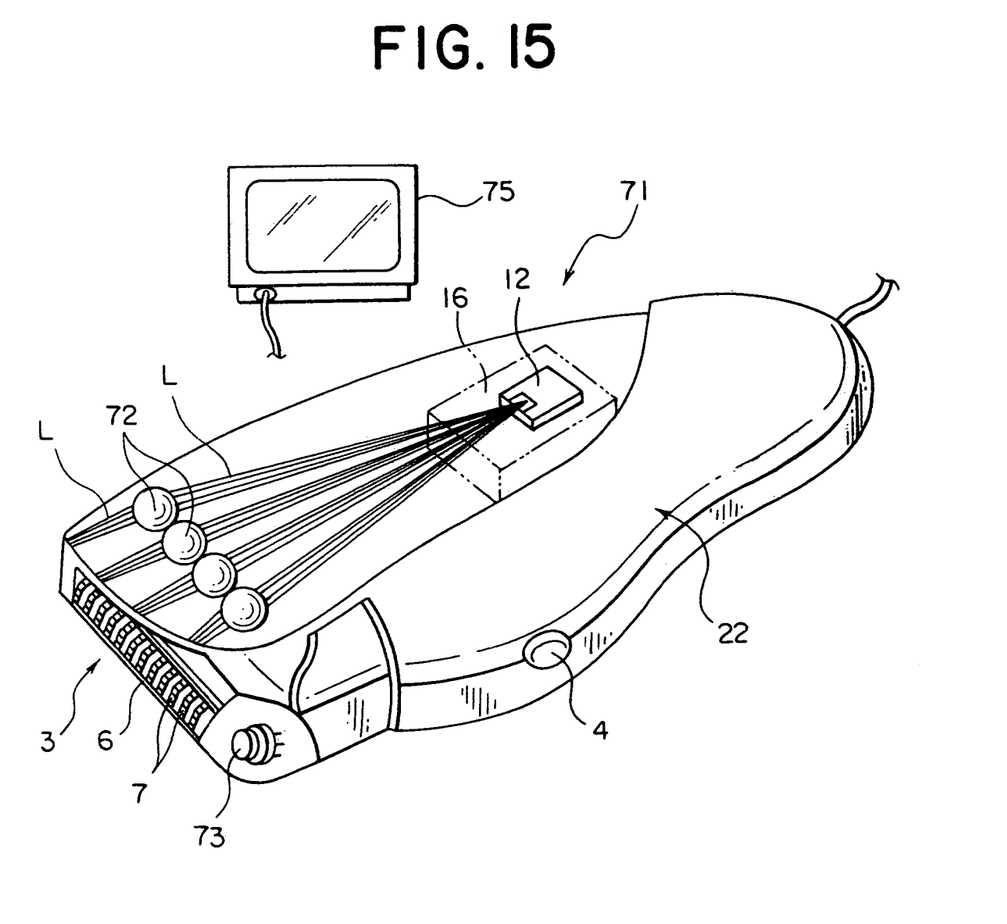
FIG. 15 is a perspective diagram showing the laser depilator according to a fourth embodiment of the invention.

FIG. 15 is a perspective diagram showing a laser depilator 71 according to the fourth embodiment of the present invention.

The laser depilator 71 according to this embodiment has plural spherical lenses 72 arranged in proximity to the tweezer head unit 3. As the individual spherical lens 72a forms a laser light condensing spots, laser light L irradiated from the laser diode 12 is substantially divided into plural luminous fluxes, and the irradiation range of the laser light L is expanded. Thus, a high-efficiency laser depilation treatment can be realized by a simple structure.

Here, the front 6 of the tweezer head unit 3 serves as a spacer and functions as a positioning means for keeping a prescribed distance between the skin surface and the spherical lens 42 for irradiation of the laser light L to the skin surface. Thus, a spot size of the laser light L irradiated to the skin surface, namely an amount of energy of the laser light L, can be controlled. The laser depilator 71 is further provided with an image pickup device 73 such as a CCD camera or a CMOS camera for taking a picture of the front of the tweezer head unit 3 contacted to the skin surface and a TV monitor 75 for displaying an image taken by the image pickup device 73 and magnified through a magnifying lens (not shown) or the like.

Therefore, the laser depilator 71 can be moved while watching the magnified image of the depilation portion displayed on the TV monitor 75, so that the laser light can be irradiated accurately to the target depilation portion. Thus, the depilatory effect is enhanced, the depilation treating efficiency is improved, and the time and labor required for the depilation treatment can be reduced. The configuration using the above image pickup device can also be applied to other embodiments.

Other Embodiments

The present invention has been described specifically with reference to the individual embodiments, but it is to be understood that the present invention is not limited to the specific embodiments thereof illustrated herein, and various modifications may be made without deviating from the spirit and scope of the invention.

For example, a Peltier element may be used for the tweezer head unit 3 or the shaving head unit 8 to be contacted to the skin surface to cool the skin surface irradiated with laser light so to ease a pain. Conversely, the skin surface may be warmed by the Peltier element to open hair pores so to irradiate laser light into hair roots securely, thereby improving the depilatory effect.

Besides, a mechanism of sucking the skin surface irradiated by laser light may be added to enlarge the hair pores in the same way so as to enhance the depilatory effect.

INDUSTRIAL APPLICABILITY

The laser depilator according to the present invention can efficiently remove hairs and irradiates laser light to hair roots and can be produced commercially.

What is claimed is:

1. A laser depilator, comprising:
   a hair removing unit for removing hairs from skin, the hair removing unit comprising a tweezer head unit and a shaving head unit which are provided at the same end of the hair removing unit such that the shaving head unit can cover the tweezer head unit;
   a light source for irradiating laser light; and
   a lens for irradiating the skin with the irradiated laser light while deforming a shape of a beam of the laser light to conform to a shape of a region of the skin from which hairs are removed by the hair removing unit,
   wherein the lens comprises a cylindrical lens, a semicylindrical lens, or an ellipsoidal lens, so that the laser light can be irradiated through a side surface of the lens perpendicular to an axial direction of the lens to conform to the shape of the region of the skin from which the hairs are removed.

2. The laser depilator according to claim 1, wherein the hair removing unit includes at least one shaving mechanism for shaving the hairs or a tweezing mechanism for tweezing the hairs.

3. The laser depilator according to claim 1, wherein the hair removing unit is detachable.

4. The laser depilator according to claim 1, further comprising:
   a movement detection unit for detecting a travel distance of the laser depilator on the skin; and
   an irradiation quantity control unit for controlling a quantity of the laser light irradiated from the light source in accordance with the travel distance detected by the movement detection unit.

5. The laser depilator according to claim 1, further comprising:
   a recovery vessel for recovering the hairs removed from the skin by the hair removing unit.

6. The laser depilator according to claim 1, further comprising:
   a grip portion for holding the laser depilator; and
   an operation unit disposed in proximity to the grip portion for operating the irradiation of the laser light from the light source and the hair removing unit.

7. The laser depilator according to claim 1, wherein the hair removing unit includes a plurality of blades.

8. The laser depilator according to claim 1, wherein a drive power supply of the depilator body is a rechargeable battery or a dry cell.

9. The laser depilator according to claim 1, further comprising:
   a depilation treatment adjusting mechanism for varying and adjusting a distribution between a drive speed of the hair removing unit and an irradiation power of the laser light by a laser irradiation mechanism.

10. The laser depilator according to claim 1, further comprising:
    an irradiation power display unit for displaying an irradiation power of the laser light irradiated from the light source.

* * * * *